United States Patent
Ozasa et al.

(10) Patent No.: US 9,551,657 B2
(45) Date of Patent: Jan. 24, 2017

(54) SAMPLE ANALYZER AND SAMPLE ANALYZING METHOD

(71) Applicant: Sysmex Corporation, Kobe-shi, Hyogo (JP)

(72) Inventors: Masatsugu Ozasa, Kobe (JP); Mitsumasa Sakamoto, Kobe (JP); Masanori Kawano, Kobe (JP)

(73) Assignee: Sysmex Corporation (JP)

( * ) Notice: Subject to any disclaimer, the term of this patent is extended or adjusted under 35 U.S.C. 154(b) by 0 days.

(21) Appl. No.: 14/634,022

(22) Filed: Feb. 27, 2015

(65) Prior Publication Data

US 2015/0247802 A1  Sep. 3, 2015

(30) Foreign Application Priority Data

Feb. 28, 2014  (JP) .................. 2014-39570

(51) Int. Cl.

| | |
|---|---|
| *G01N 21/53* | (2006.01) |
| *G01N 15/14* | (2006.01) |
| *G01N 21/64* | (2006.01) |
| *G01N 35/10* | (2006.01) |
| *G01N 15/00* | (2006.01) |
| *G01N 15/10* | (2006.01) |

(52) U.S. Cl.
CPC .......... *G01N 21/532* (2013.01); *G01N 15/147* (2013.01); *G01N 15/1429* (2013.01); *G01N 21/645* (2013.01); *G01N 35/1095* (2013.01); *G01N 2015/008* (2013.01); *G01N 2015/1006* (2013.01); *G01N 2015/1402* (2013.01); *G01N 2015/1477* (2013.01); *G01N 2021/6439* (2013.01)

(58) Field of Classification Search
CPC ........ G01N 35/0098; G01N 1/31; G01N 1/38; G01N 2035/00435; G01N 2035/00752; G01N 2035/00851; G01N 2035/0413; G01N 2035/0415; G01N 2035/0436; G01N 2035/0465; G01N 2035/0475; G01N 2035/1013
See application file for complete search history.

(56) References Cited

U.S. PATENT DOCUMENTS

| | | |
|---|---|---|
| 5,325,168 A | 6/1994 | Nakamoto et al. |
| 5,888,823 A | 3/1999 | Matsumoto et al. |
| 5,891,733 A | 4/1999 | Inoue |

(Continued)

FOREIGN PATENT DOCUMENTS

WO  WO 2014/133160 A1  9/2014

*Primary Examiner* — Michael P Stafira

(74) *Attorney, Agent, or Firm* — Brinks Gilson & Lione

(57) ABSTRACT

Disclosed is a sample analyzer which comprises: a sample preparing section configured to prepare a measurement sample by mixing a sample and a nucleic acid staining reagent; an optical detector configured to irradiate light on cells contained in the measurement sample, receive fluorescent light given off by the irradiated cells, and output fluorescent light signals; a signal processing section which obtains fluorescent light intensity and fluorescence pulse area of the cells from the fluorescent light signals output by the optical detector; and an information processing section configured to detect white blood cells contained in the measurement sample based on the fluorescence pulse area, and detect bacteria contained in the measurement sample based on the fluorescent light intensity.

19 Claims, 20 Drawing Sheets

(56) References Cited

U.S. PATENT DOCUMENTS

| | | | |
|---|---|---|---|
| 5,891,734 A * | 4/1999 | Gill | B01F 5/0453 |
| | | | 422/63 |
| 2002/0141902 A1 | 10/2002 | Ozasa et al. | |
| 2006/0073601 A1 | 4/2006 | Kawashima et al. | |
| 2009/0091746 A1 | 4/2009 | Fukuda et al. | |
| 2013/0316444 A1 | 11/2013 | Tanaka et al. | |

* cited by examiner

SAMPLE ANALYZER AND SAMPLE ANALYZING METHOD

CROSS REFERENCE TO RELATED APPLICATIONS

This application claims priority from prior Japanese Patent Applications No. 2014-039570, filed on Feb. 28, 2014, entitled "SAMPLE ANALYZER AND SAMPLE ANALYZING METHOD", the entire contents of which are incorporated herein by reference.

FIELD OF THE INVENTION

The present invention relates to a sample analyzer and sample analyzing method for analyzing samples by measuring measurement samples prepared by mixing reagent and sample such as urine or body fluid.

BACKGROUND

Sample analysis by analyzing the components contained in a sample such as urine or blood collected from a living body is widely performed in the field of clinical examinations, and sample analyzers that automate the sample analysis process have come into use in recent years.

U.S. Patent Publication No. 2009/091746 discloses a cell analyzer that analyzes cells by the flow cytometry method. The cell analyzer causes a measurement sample containing stained nucleic acid to flow through a flow cell and which is irradiated by laser light that forms a beam spot that is 3 to 8 μm in diameter in the flow direction of the measurement sample flowing through the flow cell, and uses the pulse area (integral value) of the resulting fluorescent light signal to classify cells with a nucleus 10 to 15 μm in size as abnormal cells, and classify cell with a nucleus 5 to 7 μm in size as normal cells.

Urine and body fluids may contain small cells such as bacteria in addition to white blood cells, epithelial cells, and atypical cells which are relatively larger. For example, white blood cells have a diameter of approximately 10 to 15 μm, and the diameter of the nucleus is about 10 μm. In contrast, the diameter of a bacterium is only approximately 0.4 to 2 μm. That is, a bacterium is much smaller than the nucleus of a white blood cell.

Although the cell analyzer disclosed in U.S. Patent Publication No. 2009/091746 is suitable for analyzing body fluids which contain large cells, it is unsuitable for analyzing samples which contain cells in a broad range of sizes from large cells to small cells as in the case of urine and body fluids.

It is desired to accurately analyze samples such as urine and body fluids which contain cells in a broad range of sizes from large cells to small cells.

SUMMARY OF THE INVENTION

The scope of the invention is defined by the appended claims, and not by any statements within this summary.

A first aspect of the present invention relates to a sample analyzer. The sample analyzer comprises: a sample preparing section configured to prepare a measurement sample by mixing a sample and a nucleic acid staining reagent; an optical detector configured to irradiate light on cells contained in the measurement sample, receive fluorescent light given off by the irradiated cells, and output fluorescent light signals; a signal processing section which obtains fluorescent light intensity and fluorescence pulse area of the cells from the fluorescent light signals output by the optical detector; and an information processing section configured to detect white blood cells contained in the measurement sample based on the fluorescence pulse area, and detect bacteria contained in the measurement sample based on the fluorescent light intensity.

A second aspect of the present invention relates to a sample analyzer. The sample analyzer comprises: a sample preparing section configured to prepare a measurement sample by mixing a sample and a nucleic acid staining reagent; a measuring section which comprises a light source and a flow cell, and forms a sample flow of the measurement sample within the flow cell irradiated by light from the light source to obtain fluorescent light intensity and florescence pulse area of cells contained in the measurement sample, and parameters reflecting size or nuclear diameter of the cells contained in the measurement sample; and an information processing section configured to identify a type of cell having parameters above a predetermined value based on the fluorescence pulse area, and identify a type of cell with parameters below the predetermined value based on the fluorescent light intensity.

A third aspect of the present invention relates to a sample analyzing method. The sample analyzing method comprises: preparing a measurement sample by mixing a sample and a nucleic acid staining reagent; flowing the prepared measurement sample through a flow cell and irradiating light on the flowing measurement sample in the flow cell; outputting fluorescent light signals corresponding to fluorescent light given off by the cells in the measurement sample irradiated by light; obtaining fluorescent light intensity and fluorescence pulse area of the cells from the fluorescent light signals; detecting white blood cells contained in the measurement sample based on the fluorescence pulse area; and detecting bacteria contained in the measurement sample based on the fluorescent light intensity.

DETAILED DESCRIPTION OF THE PREFERRED EMBODIMENTS

The preferred embodiments of the present invention are described hereinafter with reference to the drawings.
<Urine Sample Analyzer Structure>

The present embodiment is described in terms of a urine sample analyzer which analyzes the material components in urine. The urine sample analyzer of this embodiment takes the urine sample into the analyzer to analyze the material components (red blood cells, white blood cells, epithelial cells, casts, bacteria and the like).

Figure 1:
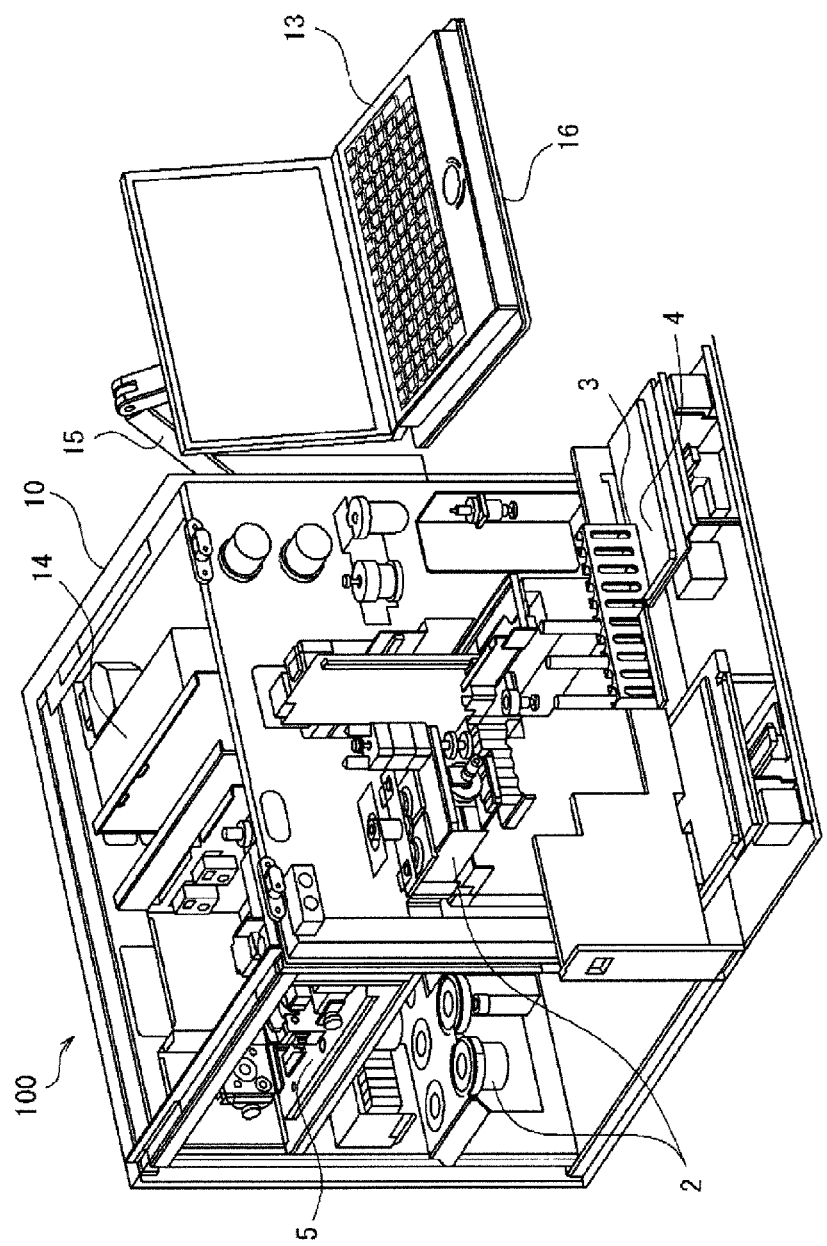
FIG. 1 is a perspective view showing the general structure of an embodiment of the urine sample analyzer.

FIG. 1 is an external perspective view showing the structure of the urine analyzer of the present embodiment. In FIG. 1, the urine sample analyzer 100 is provided with a measuring section 10, and an information processing section 13. The measuring section 10 has a sample preparing section 2 for preparing measurement sample, a rack table 4 for transporting sample racks (with upright test tubes) 3, optical detector 5 for detecting information of the material components from the measurement sample, and a circuit section 14. A support table 16 is mounted on the side surface of the cabinet through an arm 15, and the information processing section 13 is installed on the support table 16. The information processing section 13 is connected to the circuit section 14 of the measuring section 10 so as to be capable of data communications.

Figure 2:
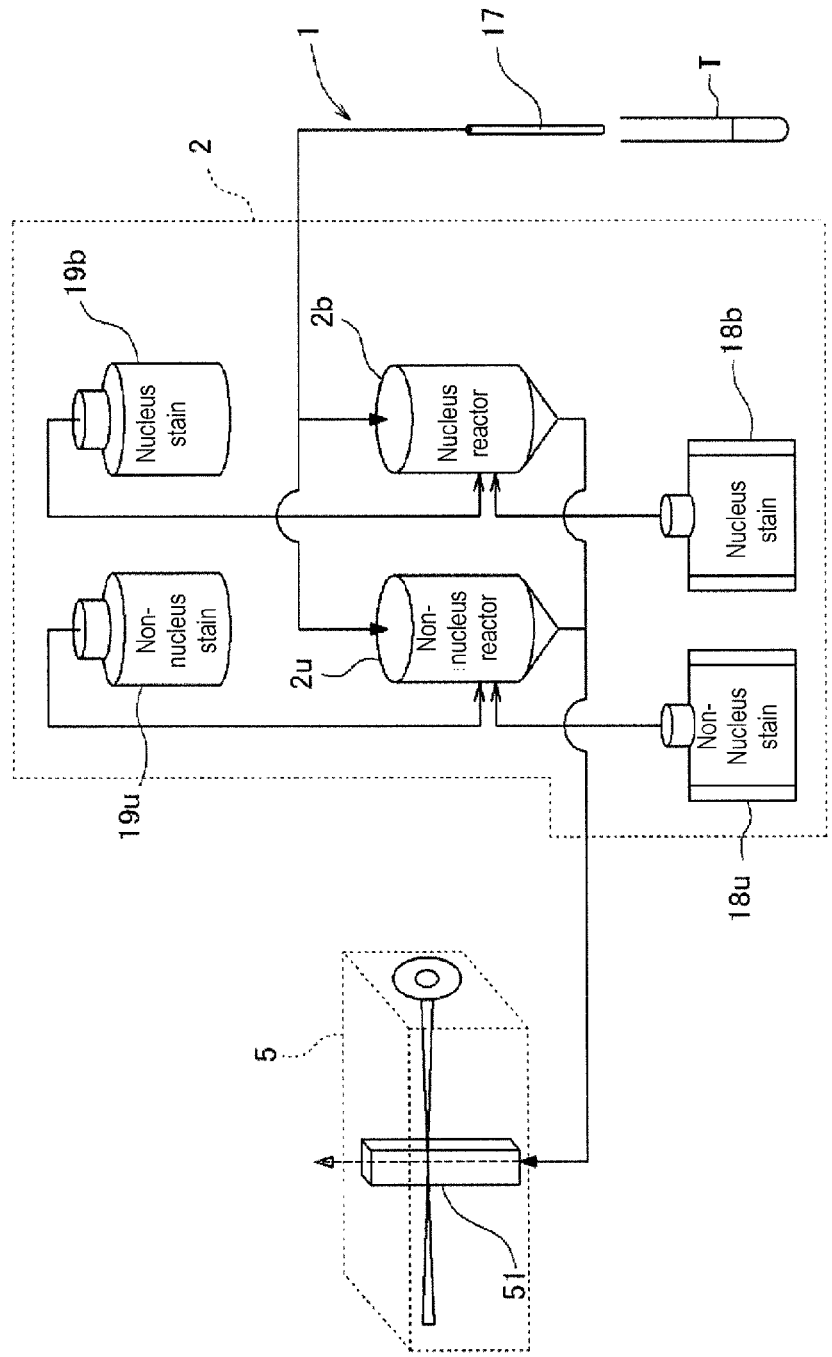
FIG. 2 shows the schematic functional structures of the sample preparing section and the optical detector.

FIG. 2 shows the schematic functional structures of the sample preparing section 2 and the optical detector 5. In the drawing, the urine sample placed in the test tube T is suctioned by a syringe pump (not shown in the drawing) using the suctioning tube 17, and subsequently dispensed to the sample preparing section 2 by the sample distributing unit 1. In the present embodiment, the sample preparing section 2 is provided with a reaction tank 2u and reaction tank 2b, and the sample distributing unit 1 distributes a fixed quantity of sample aliquot to the reaction tank 2u and the reaction tank 2b, respectively.

In the reaction tank 2u, the distributed aliquot is mixed with diluting liquid 19u and staining liquid 18u. The material components in the sample are therefore stained by the dye contained in the staining liquid 18u. The mixture prepared in the reaction tank 2u is used to analyze particles ("non-nucleated components") which lack a nucleus, that is, red blood cells and casts in the urine. The mixture prepared in reaction tank 2u is referred to as the "first measurement sample."

In the reaction tank 2b, the distributed aliquot is mixed with diluting liquid 19b and staining liquid 18b. The material components in the sample are therefore stained by the dye contained in the staining liquid 18b. The mixture prepared in the reaction tank 2b is used to analyze urinary components which have a nucleic acid, that is, bacteria and cells having a nucleus such as white blood cells, epithelial cells and fungi in the urine. Hereinafter, the urinary components having a nucleic acid are referred to as "nucleated components" The mixture prepared in reaction tank 2b is referred to as the "second measurement sample."

A tube extends from the reaction tanks 2u and 2b to the flow cell 51 of the optical detector 5, and the measurement samples prepared in the reactions tanks 2u and 2b are supplied to the flow cell 51. Among the two types of measurement sample prepared as described above, the first measurement sample of the reaction tank 2u is first supplied to the optical detector 5, then the second measurement sample of the reaction tank 2b is subsequently supplied to the optical detector 5. The first and second measurement sample supplied to the optical detector 5 are formed into a narrow flow encapsulated in sheath fluid in the flow cell 51, and irradiated by laser light. This operation is performed automatically under the control of a microcomputer 11 (control device) which operates pumps and electromagnetic valves which are not shown in the drawings.

The staining liquid 18b contains dye to stain the nucleic acid. More specifically, the staining liquid 18b contains a fluorescent dye which binds to the minor groove, and intercalator to specifically stain the nucleic acid. Well known dyes such as cyanine dyes, acridine dyes, and phenanthridium dyes may be used as the intercalator. SYBR green I, and thiazole orange are examples of useful cyanine dyes. Acridine orange is an example of a useful acridine dye. Propidium iodide and ethidium bromide are examples of useful phenanthridium dyes. DAPI and Hoechst are well known examples of dyes binding to the minor groove. Hoechst 33342 and Hoechst 33258 arc examples useful dyes which bind to the minor groove. In the present embodiment, cyanine intercalator is preferable, and SYBR green I and thiazole orange are particularly preferred.

The diluting liquid 19b contains hemolytic agent. More specifically, the diluting liquid 19b contains a cationic surfactant to cause the staining liquid 18b to proceed through the membrane by injuring the cell membrane, and contract the contaminants such as red blood cell debris resulting from lysed red blood cells. Note that the type of surfactant is not limited to cationic surfactant, inasmuch as nonionic surfactant also may be used. The material components containing nucleic acid in the urine are stained to an extend corresponding to their structure and characteristics.

The red blood cells in the second measurement sample are lysed because the diluting liquid 19b contains hemolytic agent, and the cells which have nucleic acid such as white blood cells can be measured with high precision. The nucleic acid stain is effective because the diluting liquid containing hemolytic agent is used to injure the cell membrane. This also improves measurement accuracy of cell having nucleic acid.

The staining liquid 18u contains a fluorescent dye which stains the material components that do not have nucleic acid.

The diluting liquid 19u is a reagent composed mainly of buffering agent. Diluting liquid 19u contains osmotic pressure compensating agent to obtain fluorescent light signals which are stabilized without lysing the red blood cells.

Figure 3:
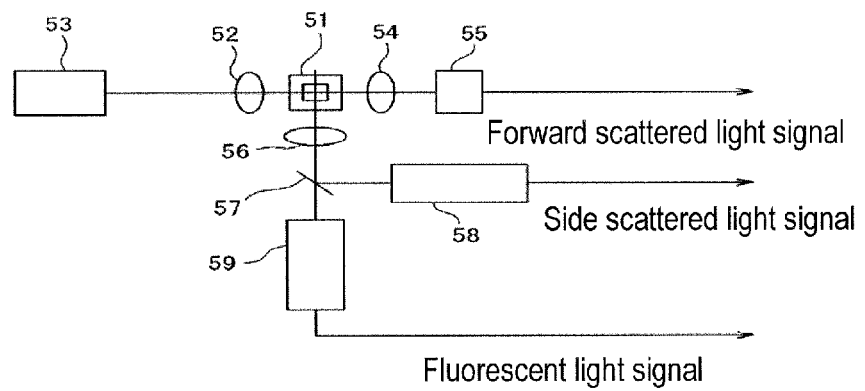
FIG. 3 shows the structure of the optical detector.

FIG. 3 shows the structure of the optical detector 5. A condenser lens 52 converges laser light emitted from a semiconductor light source 53 onto a flow cell 51.

The light emitted from the light source 53 is formed in a flat beam spot on the sample flowing within the flow cell 51 via the condenser lens 52. The beam spot has a diameter of 3 to 8 μm in the sample flow direction. The diameter of the beam spot preferably is 3.5 to 7.5 μm, and more preferably is 4 to 7 μm, in the sample flow direction so that the laser light stably irradiates the cell nucleus. The beam spot has a diameter of 4 to 7 μm in the sample flow direction in the present embodiment.

A collecting lens 54 condenses the forward scattered light given off by the material components in the measurement sample on a first scattered light receiver 55. A collecting lens 56 condenses the side scattered light and fluorescent light given off from the material components on a dichroic mirror 57. The dichroic mirror 57 reflects the side scattered light to a second scattered light receiver 58, which is a photomultiplier. The first scattered light receiver 55, second scattered light receiver 58, and a fluorescent light receiver 59 convert the optical signals to electrical signals, and respectively output forward scattered light signals (referred to as "FSC" below), side scattered light signals (referred to as "SSC" below), and fluorescent light signals (referred to as "FL" below). The fluorescent light receiver 59 outputs fluorescent light signals of both low and high sensitivity by switching the drive voltage. Switching the sensitivity is controlled by a microcomputer 11 which is described later.

Note that although a gas laser also may be used as the light source rather than the semiconductor laser, a semiconductor laser is preferable as the light source from the perspectives of low cost, compactness, and low power consumption.

Figure 4:
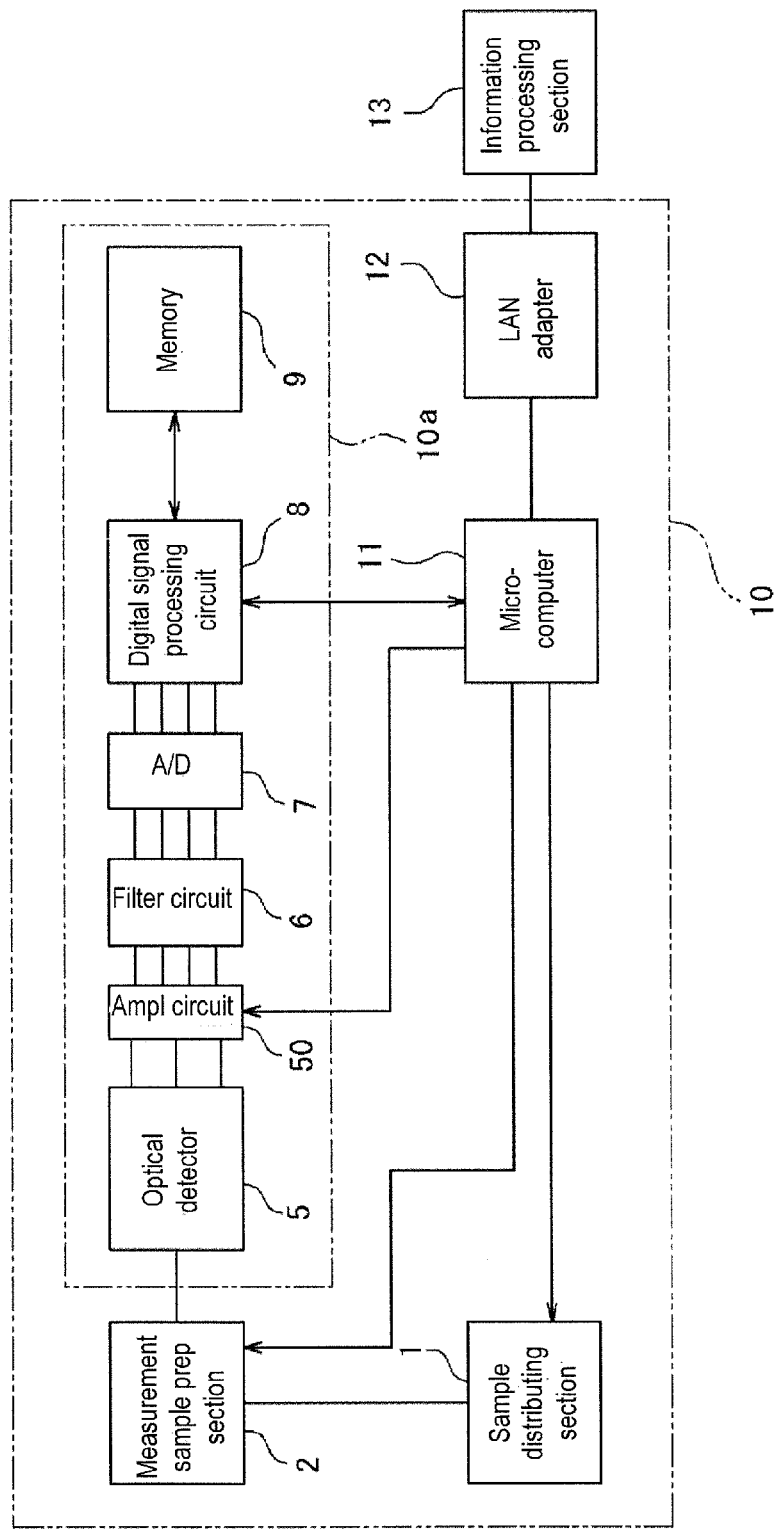
FIG. 4 is a block diagram showing the structure of an embodiment of the urine sample analyzer.

FIG. 4 is a block diagram showing the structure of the urine analyzer 100. The measuring section 10 is configured by the previously mentioned sample distributing unit 1, sample preparing section 2, and optical detector 5, an amplification circuit 50 which amplifies the output signals of the optical detector 5, filter circuit 6 which performs a filtering process on the output signals from the amplification circuit 50, an A/D converter 7 which converts the analog output signals of the filter circuit 6 to digital signals, a digital signal processing circuit 8 which performs a waveform process on the output signals of the filter circuit 6, a memory 9 which is connected to the digital signal processing circuit 8, a microcomputer 11 which is connected to the sample distributing unit 1, sample preparing section 2, amplification circuit 50, and digital signal processing circuit 8, and a LAN adapter 12 which is connected to the microcomputer 11. The information processing section 13 is connected to the measuring section 10 via a LAN cable to the LAN adapter 12. The information processing section 13 analyzes the measurement data obtained by the measuring section 10. The optical detector 5, amplification circuit 50, filter circuit 6, A/D converter 7, digital signal processing circuit 8, and memory 9 configure the measuring section 10a which measures the measurement sample and generates measurement data.

The optical detector 5 amplifies each signal FSC, SSC, and FL by preamp. Each amplified signal is input to the amplification circuit 50. The FL signal channel extending from the output side of the optical detector 5 is branched between the preamp and the amplification circuit 50. One signal channel is connected to the high amplification amplifier (high amp) of the amplification circuit 50. The other signal channel is connected to the low amplification amplifier (low amp). Accordingly, a signal FLH amplified at high sensitivity, and a FLL signal amplified at low sensitivity are obtained from the FL signal corresponding to a single particle. The FL signal input to the high amp is designated an "FLH" signal, and the FL signal input to the low amp is designated an "FLL" signal.

The amplification circuit 50 amplifies the four types of signals FSC, SSC, FLH, and FLL according to a set gain. The amplification circuit 50 allows a plurality of different gains to be set. The microcomputer 11 controls the sensitivity of the amplification circuit 50 by setting the gain of the amplification circuit 50.

Figure 5:
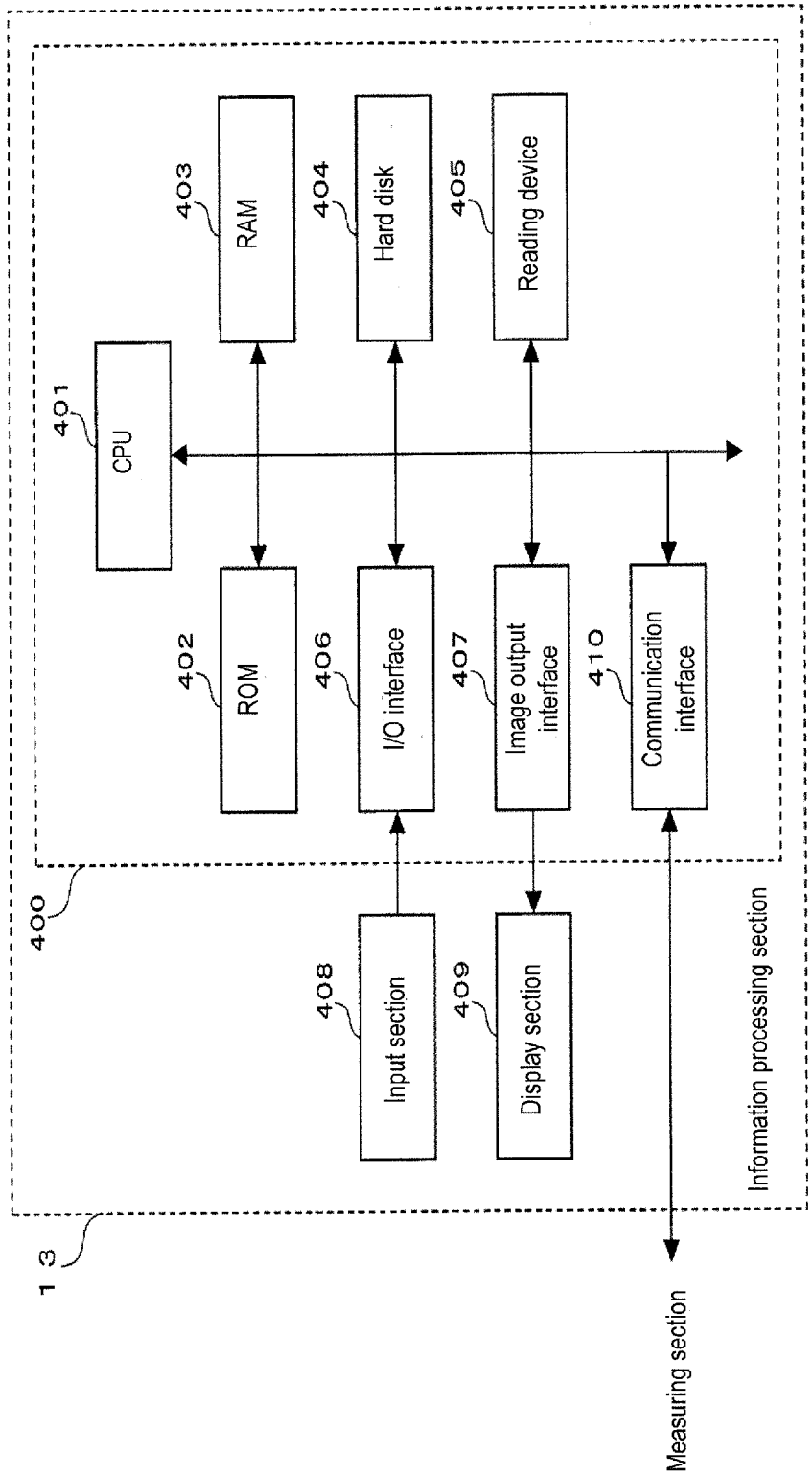
FIG. 5 is a block diagram showing the structure of the information processing section.

FIG. 5 is a block diagram showing the structure of the information processing section 13. The information processing section 13 is a personal computer. The information processing section 13 is configured by a main body 400, input unit 408, and display unit 409. The main body 400 has a CPU 401 ROM 402, RAM 403, hard disk 404, reading device 405, I/O interface 406, image output interface 407, and communication interface 410.

The CPU 401 is capable of executing a computer program stored in the ROM 402 and a computer program loaded in the RAM 403. The RAM 403 is used when reading the computer program stored in the ROM 402 and on the hard disk 404. The RAM 403 is also used as the work area of the CPU 401 when the CPU 401 executes the computer programs.

An operating system and application programs, as well as the data used when executing the operating system and application programs that are executed by the CPU 401, are installed on the hard disk 404. A computer program for analyzing measurement data received from the measuring section 10 and outputting analysis results is installed on the hard disk 404.

The reader 405 is a CD drive or DVD drive capable of reading computer programs and data recorded on a recording medium. The I/O interface 406 is connected to the input section 408 configured by a mouse and keyboard, and the user operates the input section 408 to input data to the information processing section 13. The image output interface 407 is connected to the display section 409 configured by a liquid crystal display or the like, and the image output interface 407 outputs image signals corresponding to the image data to the display section 409. The display section 409 displays images based on the input image signals. The information processing section 13 also is connected to the measuring section 10 through a communication interface 410, and data are sent and received through the communication interface 410 to/from the measuring section 10.

<Urine Analyzer Operation>

The operation of the urine sample analyzer of the present embodiment is described below.

Figure 6:
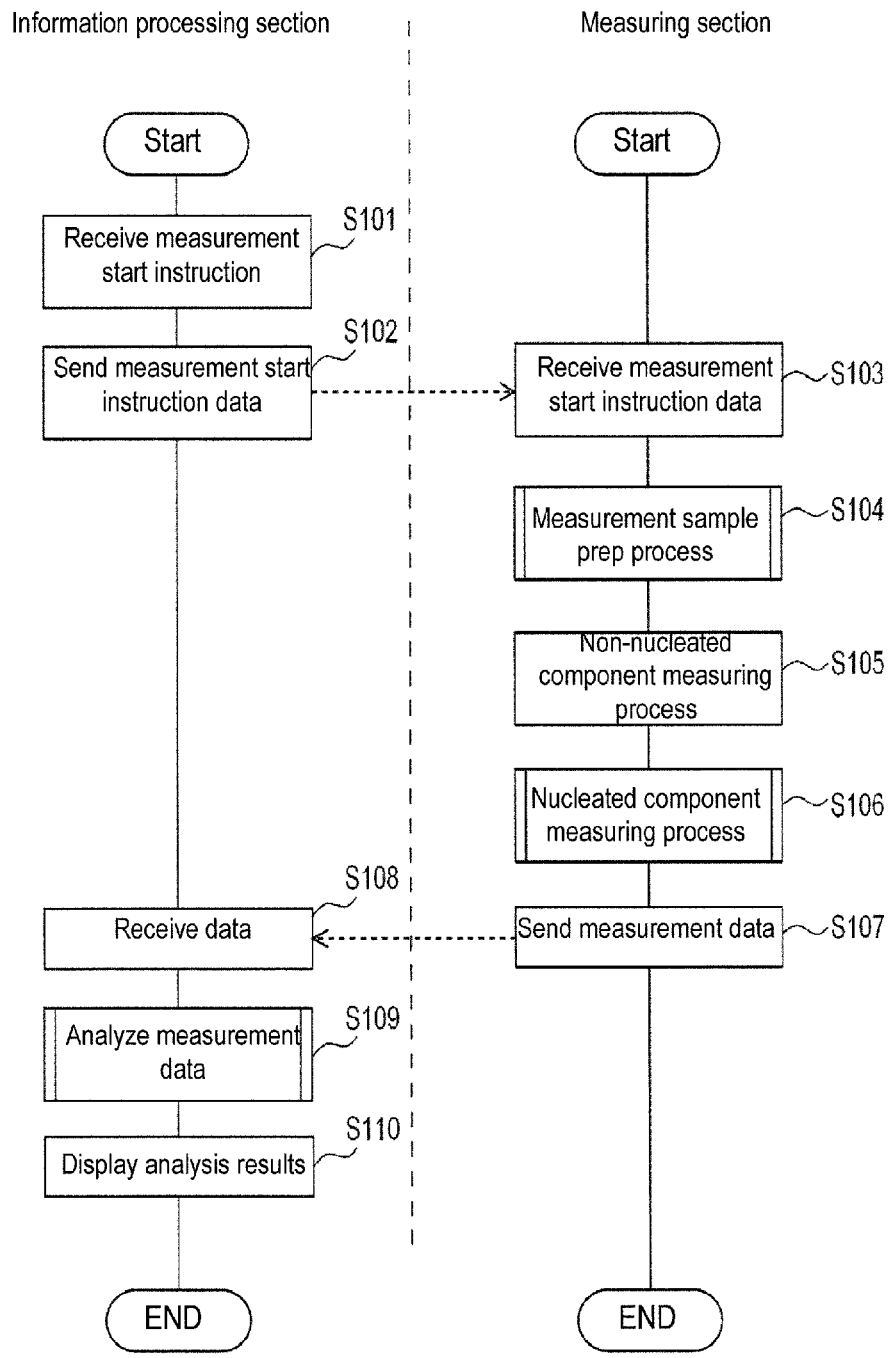
FIG. 6 is a flow chart showing the sequence of the sample measurement process performed by the urine sample analyzer of the embodiment.

FIG. 6 is a flow chart showing the sequence of the sample measurement process performed by the urine sample analyzer 100. The user first inputs a measurement execution instruction to the information processing section 13 through the input section 408 (step S101). When the instruction is received, the CPU 401 sends instruction data to start a measurement to the measuring section 10 (step S102). When the measuring section 10 receives the instruction data (step S103), the microcomputer 11 executes a measurement sample preparing process (step S104), a non-nucleated component measuring process (step S105), and a nucleated component measuring process (step S106).

Figure 7:
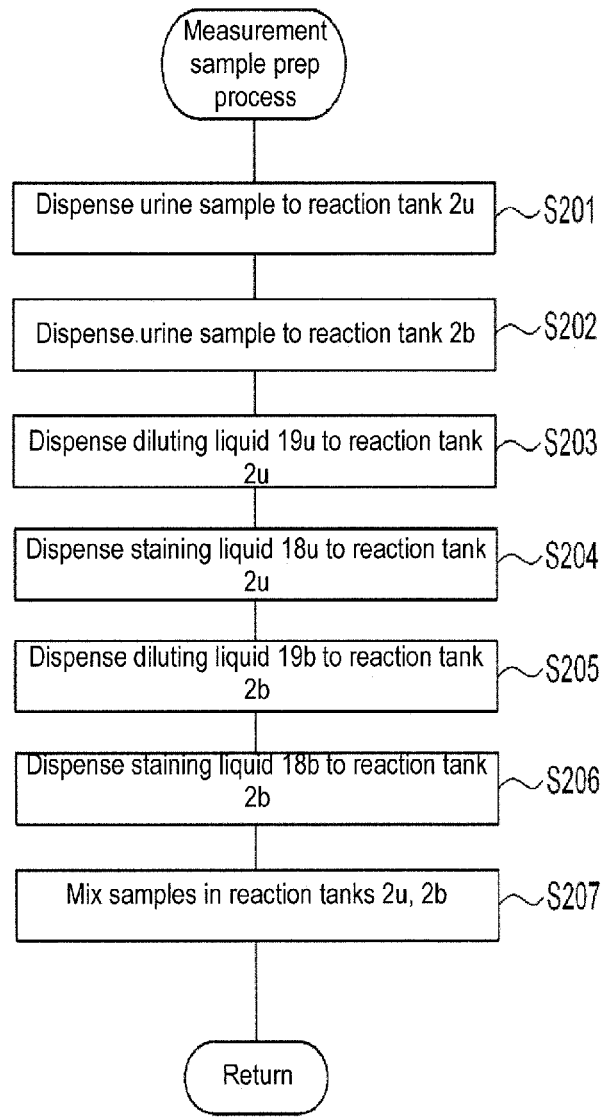
FIG. 7 is a flow chart showing the sequence of the measurement sample preparing process.

FIG. 7 is a flow chart showing the sequence of the measurement sample preparing process. In the measurement sample preparing process, microcomputer 11 first controls the sample distributing unit 1, to suction a predetermined amount from the sample container T via the suctioning tube 17, and dispense predetermined amounts of urine sample to the reaction tank 2u and reaction tank 2b, respectively.

The microcomputer 11 controls the sample preparing section 2 and executes the subsequent steps S203 through 207. In steps S203 and S204, a predetermined amount of diluting liquid 19u and a predetermined amount of staining liquid 18u are dispensed to the reaction tank 2u (steps S203 and S204). In steps S205 and S206, predetermined amounts of diluting liquid 19b and staining liquid 18b are dispensed to the reaction tank 2b (steps S205 and S206). The reaction tank 2u and reaction tank 2b are preheated to a predetermined temperature by heaters (not shown in the drawing), and the mixture in each tank is mixed by a propeller-like mixing tool (not shown) in step S207 (step S207). In this way the first measurement sample to be used for non-nucleated component measurements is prepared in the reaction tank 2u, and a second measurement sample to be used for nucleated component measurements is prepared in reaction tank 2b. When the process of step S207 ends, the microcomputer 11 returns the processing to the main routine.

In the non-nucleated component measuring process (step S 105), the first measurement sample from the reaction tank 2u is supplied together with sheath fluid to the flow cell 51 to form a sample flow in which the first measurement sample is encapsulated in sheath fluid in the flow cell 51. The formed sample flow is then irradiated by a laser beam emitted from the light source 53, which forms a beam spot on the flow cell 51. Forward scattered light, fluorescent light, and side scattered light are generated each time a particle passes through the beam spot. The forward scattered light, fluorescent light, and side scattered light is respectively received by the first scattered light receiver 55, fluorescent light receiver 59, and second scattered light receiver 58 and converted to electrical signals FSC, FLH, FLL, and SSC, which are output. The output signals FSC, FLH, FLL, and SSC are amplified by the amplification circuit 50.

The signals FSC, FLH, FLL, and SSC amplified by the amplification circuit 50 are subjected to a filtering process by the filter circuit 6, then converted to digital signals by the A/D converter 7, and the digital signals are then subjected to processing by the digital signal processing circuit 8. In this way the analysis parameters forward scattered light intensity (FSCP), forward scattered light pulse width (FSCW), fluorescent light intensity (FLHP), fluorescent light pulse width (FLLW), side scattered light intensity (SSCP) and the like are extracted for each particle passing through the flow cell 51. The analysis parameters are stored in the memory 9 as measurement data, whereupon the non-nucleated component measuring process ends.

Figure 8:
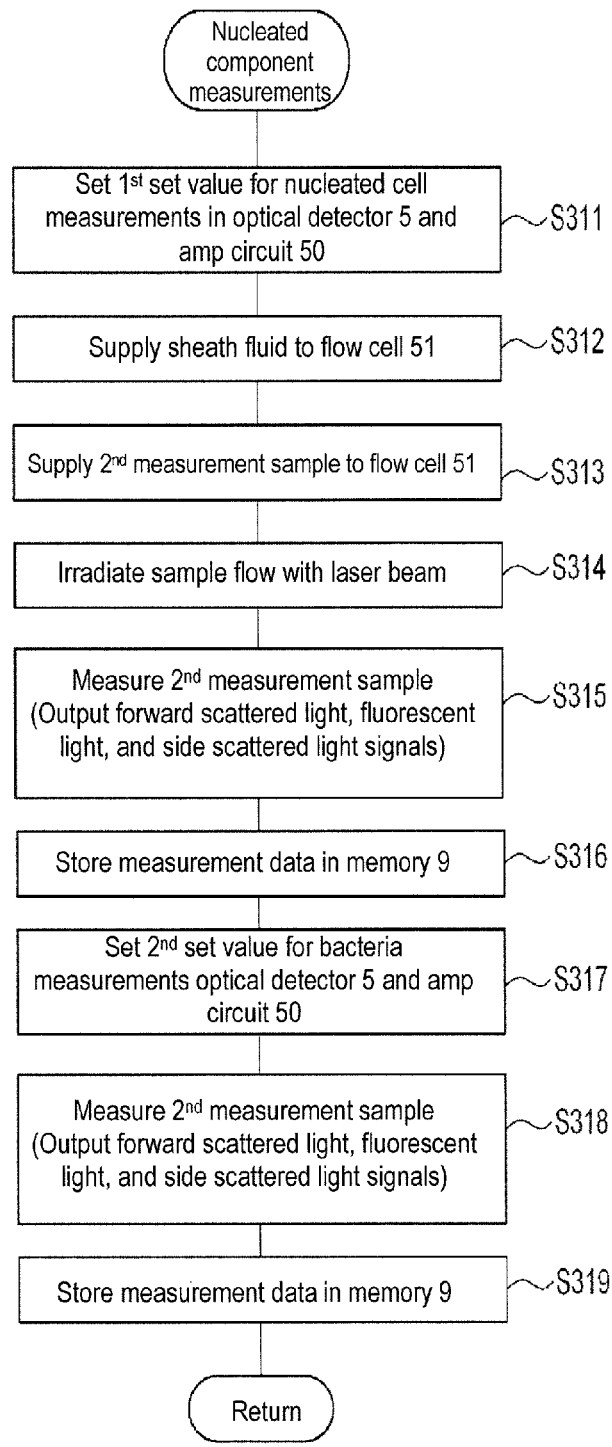
FIG. 8 is a flow chart showing the sequence of the material component measuring process.

The nucleated component measuring process (step S 106) is described below. FIG. 8 is a flow chart showing the sequence of the nucleated component measuring process. In the nucleated component measuring process, the microcomputer 11 first sets the gain of the amplification circuit 50 and the sensitivity of the first scattered light receiver 55 and the second scattered light receiver 58 at a first set value (step S311). The first set value is a value for measuring nucleated cells, which have a nucleus, such as white blood cells, epithelial cells, and fungi which are larger than bacteria. The microcomputer 11 drives a compressor (not shown in the drawing) to move the sheath fluid to the flow cell 51 (step S312). While the sheath fluid is being supplied to the flow cell 51, the microcomputer 11 drives a compressor (not shown in the drawing) to supply the second measurement sample from the reaction tank 2b to the flow cell 51 (step S313).

In this way a sample flow is formed in which the second measurement sample is encapsulated in sheath fluid in the flow cell 51. The formed sample flow is then irradiated by a laser beam emitted from the light source 53 (step S314), which forms a beam spot on the flow cell 51. Forward scattered light, fluorescent light, and side scattered light are generated each time a particle passes through the beam spot. The forward scattered light, fluorescent light, and side scattered light is respectively received by the first scattered light receiver 55, fluorescent light receiver 59, and second scattered light receiver 58 and converted to electrical signals (step S315). When converting the photoreception level of the fluorescent light receiver 59 to electrical signals, the sensitivity is determined by the first set value used for nucleated cell measurements which was set in step S311.

The first scattered light receiver 55, fluorescent light receiver 59, and second scattered light receiver 58 output electrical signals as signals FSC, FL, and SSC corresponding to the photoreception level. The optical detector 5 divides the signal FL into two signals FLH and FLL, which are input to the amplification circuit 50. The input signals arc amplified by the amplification circuit 50. The signal amplification factor of the amplification circuit 50 is determined by the first set value used for nucleated cell measurements which was set in step S311.

The first set value is a low value compared to the second set value which is described later. That is, when the first set value is set, the signal FL is amplified by a low amplification factor compared to when the second set value is set. Specifically, when the first set value is set, the fluorescent light given off by the particle is subjected to photoelectric conversion at low sensitivity by the fluorescent light receiver 59, and the converted signal is output. The signals FLH and FLL output from the optical detector 5 at this time are respectively amplified by a low amplification factor and a high amplification factor by the low amp and the high amp of the amplification circuit 5. As a result, two types of fluorescent light signals are obtained, a low sensitivity fluorescent light signal (FLL) amplified by the low amplification factor, and a first high sensitivity fluorescent light signal (referred to as "FLH1" below) amplified by the high sensitivity amplification factor.

The amplified signals FSC, FLL, FLH1, and SSC are subjected to a filtering process by the filter circuit 6, then converted to digital signals by the A/D converter 7, and the digital signals are then subjected to predetermined processing by the digital signal processing circuit 8.

The digital signal processing circuit 8 extracts parameters to be used in an analysis process from the optical signals (FSC, SSC, FLL, FLH1) by signal processing. These analysis parameters include forward scattered light intensity (referred to as "FSCP" below), forward scattered light pulse width ("FSCW" below), side scattered light intensity ("SSCP" below), low sensitivity fluorescent light intensity ("FLLP" below), low sensitivity fluorescent light pulse width ("FLLW" below), low sensitivity fluorescent light pulse area ("FLLA" below), first high sensitivity fluorescent light intensity ("FLHP1" below), first high sensitivity fluorescent light pulse width ("FLHW1"), and first high sensitivity fluorescent light pulse area ("FLHA1").

Figure 9A:
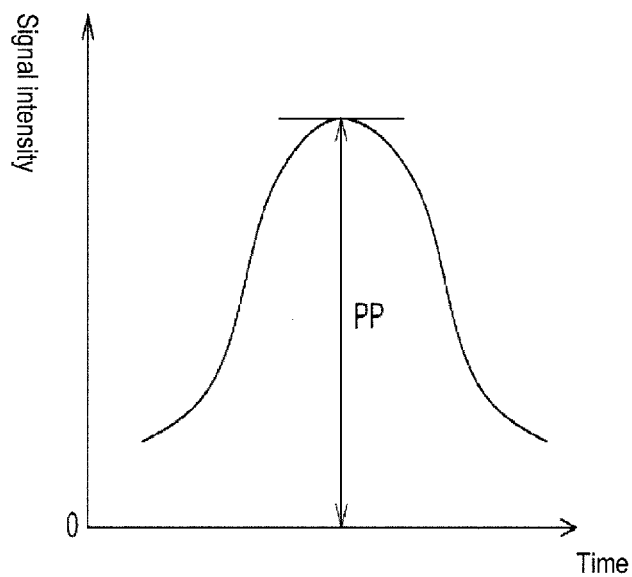
FIG. 9A is a schematic drawing describing the intensity of the optical signals.
Figure 9B:
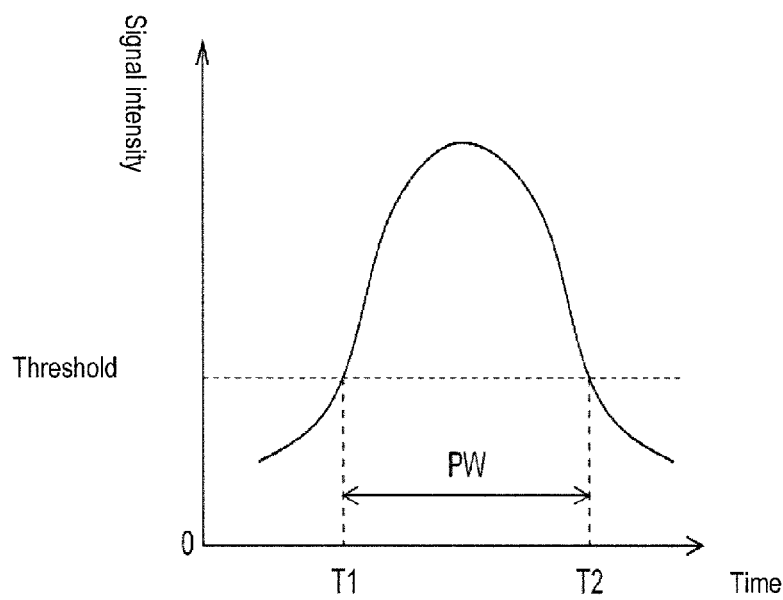
FIG. 9B is a schematic drawing describing the pulse width of the optical signals.
Figure 9C:
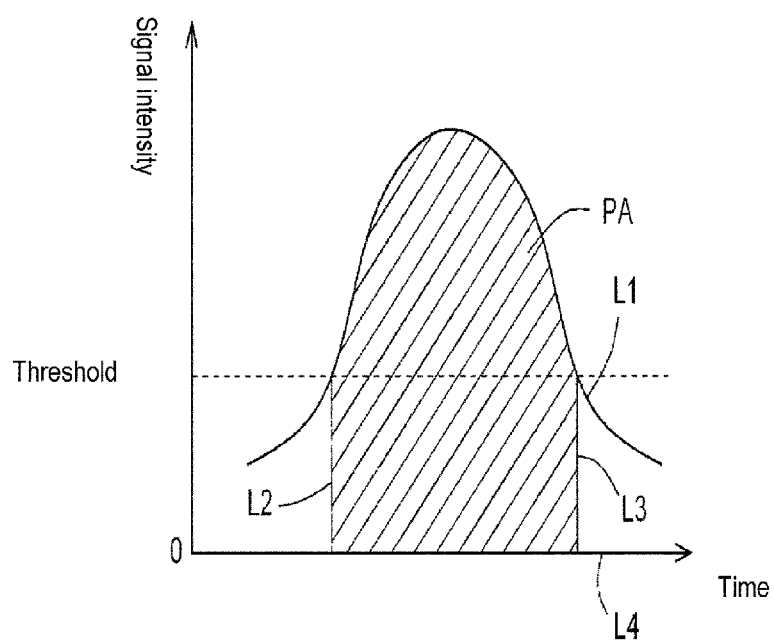
FIG. 9C is a schematic drawing describing the pulse area of the optical signals.

The extraction of analysis parameters is described below based on FIGS. 9A through 9C. There are three types of analysis parameters, which are intensity, pulse width, and pulse area for each optical signal. Intensity is represented by P. Pulse width is represented by W. Pulse area is represented by A. The intensity of the optical signals FSCP, SSCP, FLLP, and FLHP1 and the like is respectively obtained as the peak height PP of the pulse, as shown in FIG. 9A. The pulse width of the optical signals FSCW, FLLW, and FLHW1 is respectively obtained as the interval PW from the time T1 at which the pulse exceeds a predetermined threshold value to the time T2 at which the pulse drops below the threshold value, as shown in FIG. 9B. The pulse area of the optical signals FLLA and FLHA1 is respectively obtained as the area of the region (region indicated by the diagonal lines in the drawing) PA circumscribed by the signal pulse waveform line L1, straight lines L2 and L3 indicating the times the pulse height meets the predetermined threshold value, and straight line L4 indicating the value of the signal optical intensity is 0, that is, the pulse area is obtained as the time integral value of the signal intensity, as shown in FIG. 9C.

Note that the method of extracting the analysis parameters shown here is only an example, and a different extraction method may be used. The pulse area is not limited to a time integral value, and may be an approximate value insofar as the value reflects the time area under the curve of the pulse. For example, the pulse area also may be the product of the pulse width and the peak height, and also may be the area of a triangle determined from the pulse width and the peak height. Further, in the mode of extracting the time integral value, the base need not be a straight line of strength 0, and may be suitably set. For example, the predetermined threshold value may be used as the base as shown in FIG. 9C, or the pulse value when only sheath fluid flows through the flow cell 51 may be set as a standard value and used as the base.

Refer again to FIG. 8. The parameter extracted from the optical signal as described above is stored as measurement data in the memory 9 (step S316).

When a predetermined time has elapsed after the second measurement sample has started to be supplied to the flow cell 51, the microcomputer 11 changes the sensitivity of the fluorescent light receiver 59 and the gain of the amplification circuit 50 to second set values (step S317). The second set value is a value set for the measurement of bacteria.

While the fluorescent light receiver 59 and amplification circuit 50 are set the second value, the measurement of the second measurement sample is performed by the measuring section 10a (step S318). In this way the signal FL is output from the fluorescent light receiver 59 at the sensitivity set by the second set value, and the output signals of the first scattered light receiver 55, the second scattered light receiver 58, and the fluorescent light receiver 59 are amplified by the amplification circuit 50 by an amplification factor determined by the second set value.

The second set value is a high value compared to the previously mentioned first set value. That is, when the second set value is set, the signal FL is amplified by a high amplification factor compared to when the first set value is set. When the second set value is set, the photoreception sensitivity of the photoelectric conversion performed by the fluorescent light receiver 59 is set to be several times that of the first set value. The amplification factor of the amplification circuit 50 is identical to the amplification factor in the first set value. While the second set value is set, the signal FL output from the fluorescent light receiver 59 is amplified at high amp by the amplification circuit 50, and obtained as the second high sensitivity fluorescent light signal ("FLH2" below).

The sensitivity of the fluorescent light receiver 59 when the second set value is set is five-times the sensitivity of the fluorescent light receiver 59 when the first set value is set. This configuration is used because bacteria are smaller in size compared to the nucleated cells such as white blood cells and epithelial cells, so the amount of fluorescence is less compared to the nucleated cells. By increasing the sensitivity of the fluorescent light receiver 59 higher than the sensitivity used to measure nucleated cells, the sensitivity becomes suitable for bacteria and bacteria can be detected with high accuracy. Note that although only the sensitivity of the fluorescent light receiver 59 is increased to raise the magnification factor five-fold when the second set value is set in the present embodiment, the sensitivity of the fluorescent light receiver 59 and the amplification factor of the amplification circuit 50 may both be increased. For example, when the second set value is set, the sensitivity of the fluorescent light receiver 59 may be set at 2.5 times the sensitivity when the first set value is set and the amplification factor of the amplification circuit 50 may be set at double the amplification factor in the first set value.

The amplified signals FSC, FLH2, and SSC are subjected to a filtering process by the filter circuit 6, then converted to digital signals by the A/D converter 7, and the digital signals are then subjected to predetermined processing by the digital signal processing circuit 8. The signals FSCP and FSCW are extracted from the signal FSC, and the signal SSCP is extracted from the signal SSC via this signal processing. The peak value of the signal FLH2 also is extracted as the second high sensitivity fluorescence intensity (referred to as "FLHP2" below). The pulse width of the signal FLH2 is extracted as the second high sensitivity fluorescence pulse width ("FLHW2" below). The pulse area of the signal FLH2 is extracted as the second high sensitivity fluorescence pulse area ("FLHA2" below). In this way analysis parameters are obtained for each particle passing through the flow cell 51. The parameter data extracted for each particle are stored as measurement data in the memory 9 (step S319). When this process is completed, the microcomputer 11 returns the process to the main routine.

Following the nucleated component measuring process described above, the microcomputer 11 transmits the measurement data generated in the non-nucleated component measuring process and the nucleated component measuring process to the information processing section 13 (step S107), and the process ends.

Figure 10:
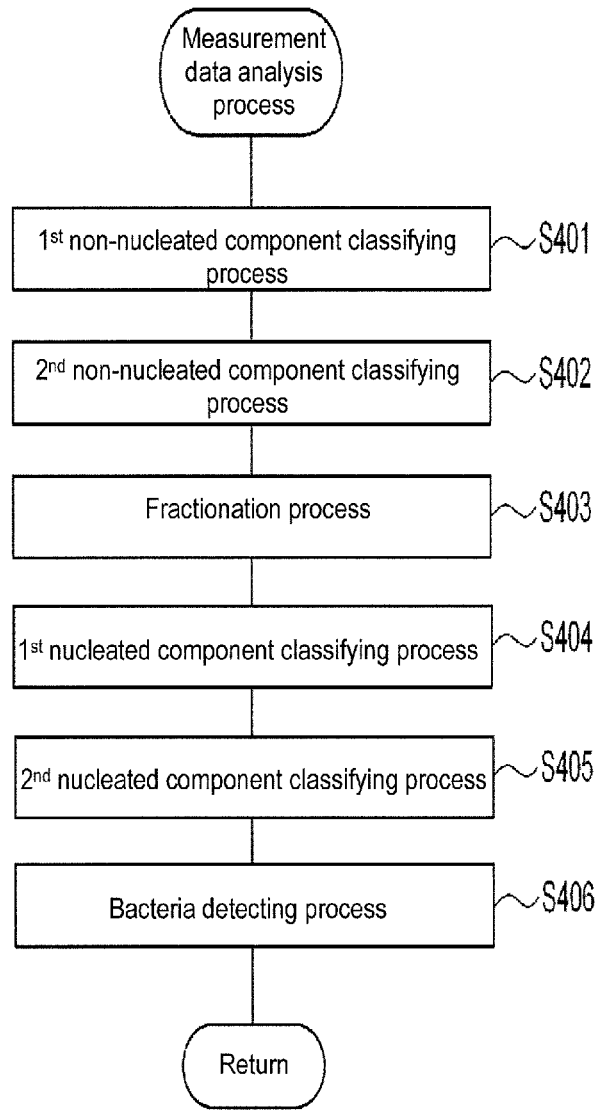
FIG. 10 is a flow chart showing the sequence of the measurement data analyzing process.

When the information processing section 13 receives the measurement data (step S108), the CPU 401 executes the measurement data analyzing process FIG. 10 is a flow chart showing the sequence of the measurement data analyzing process; The measurement data analyzing process includes a first non-nucleated component classifying process (step S401), a second non-nucleated component classifying process (step S402), a fractionation process (step S403), a first nucleated component classifying process (step S404), a second nucleated component classifying process (step S405), and a bacteria detecting process (step S406).

In the first non-nucleated component classifying process of S401, the signals FSC and FLH which were obtained by measuring the first measurement sample are used to detect and determine the respective numbers of red blood cells and crystals.

In the second non-nucleated component classifying process of S402, the signals FSC and FLL which were obtained by measuring the first measurement sample are used to detect and determine the respective numbers of casts and mucus threads.

Cells containing nucleic acid in the urine are also classified by the first nucleated component classifying process, second nucleated component classifying process, and bacteria detecting process.

Figure 11:
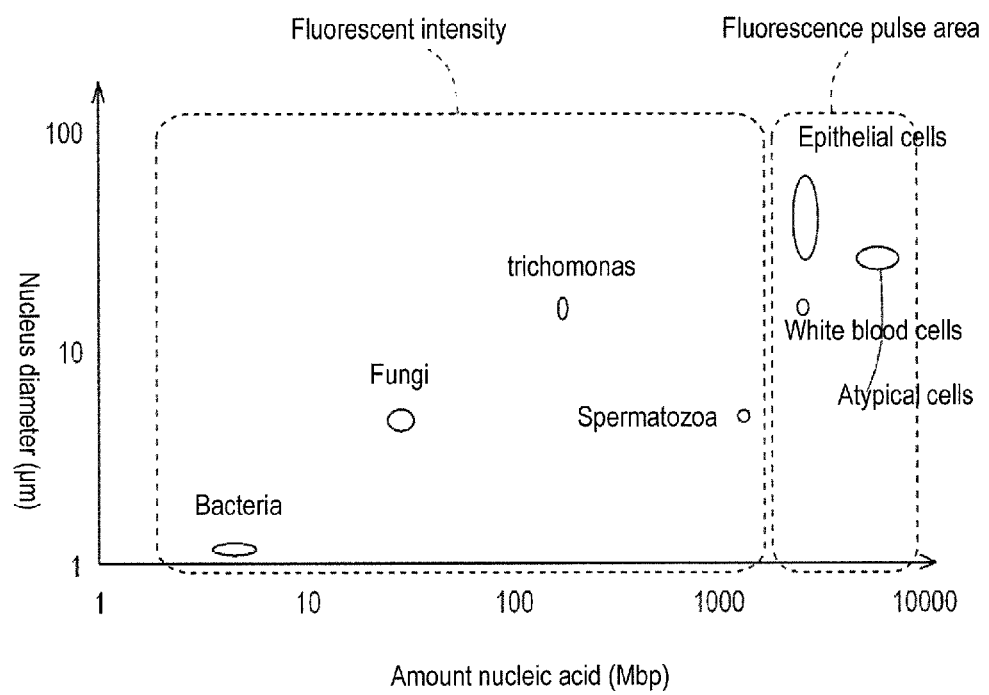
FIG. 11 is a schematic drawing describing the relationship between the amount of nucleic acid and the size of the nucleated material component in the urine.

The classification of nucleated material component by the sample analyzer of the present embodiment is described below. FIG. 11 is a schematic drawing describing the relationship between the amount of nucleic acid and the size of the nucleated material component. The horizontal axis in FIG. 11 represents the amount of nucleic acid, and the vertical axis represents the size (particle diameter) of the material component. The nucleated material component in urine listed in descending order according to the amount of nucleic acid includes atypical cells, epithelial cells, white blood cells, spermatozoa, trichomonas, fungi, and bacteria.

Among the nucleated material components, epithelial cells, atypical cells, and white blood cells are largest. Epithelial cells have a diameter of approximately 50 to 100 μm, and the nucleus diameter is approximately 10 μm. Atypical cells have a diameter of approximately 10 to 20 μm, and the nucleus diameter is approximately 10 to 15 μm. White blood cells have a diameter of approximately 10 to 15 μm, and the nucleus diameter is approximately 10 μm.

Conversely, spermatozoa, trichomonas, fungi, and bacteria are small. The head of the spermatozoa measures approximately 4 to 5 μm. Trichomonas have a diameter of approximately 7 to 15 μm, and the nucleus diameter is approximately 5 μm. Pre-emergence fungi have a diameter of approximately 3 to 8 μm, and the nucleus diameter is approximately 3 μm. Bacteria have a diameter of approximately 0.4 to 2 μm, and therefore is smaller than spermatozoa, trichomonas, and fungi. Bacteria lacks a nucleus, but does contain nucleic acid.

In the present embodiment described above, the nucleus diameter of epithelial cells, atypical cells, and white blood cells is larger than the beam spot diameter since the diameter of the beam spot formed by the light source 53 in the sample flow direction is approximately 4 to 7 μm. The head of spermatozoa, nucleus of fungi, and bacteria are smaller than the beam spot diameter.

Figure 12A:
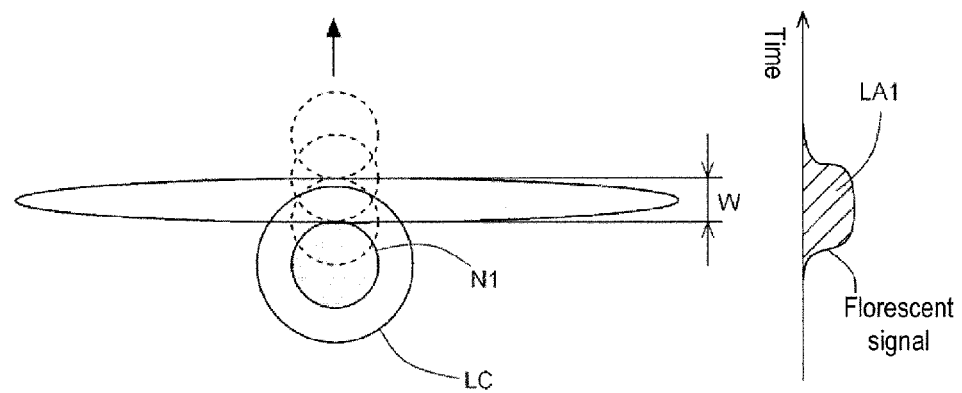
FIG. 12A is a schematic drawing describing the pulse area of the fluorescent light signals obtained from large size material components.
Figure 12B:
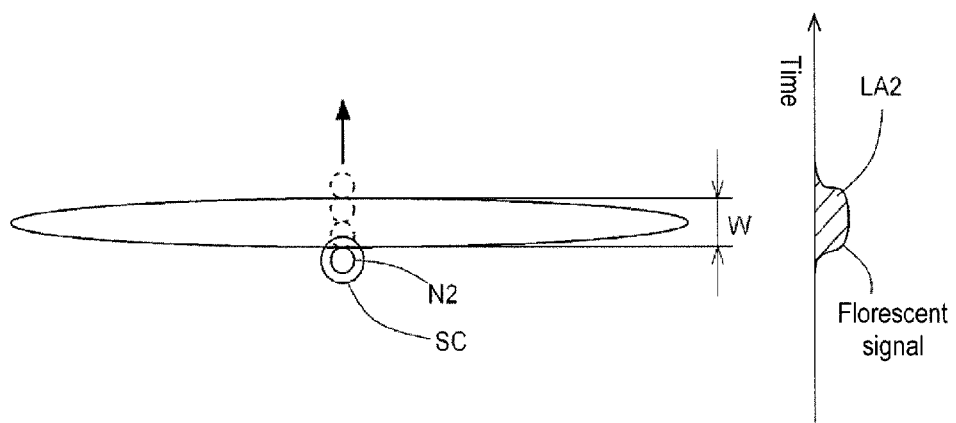
FIG. 12B is a schematic drawing describing the pulse area of the fluorescent light signals obtained from the small size material components.

FIG. 12A is a schematic view illustrating the pulse area of the fluorescent light signal obtained from large cells such as white blood cells, and FIG. 12B is a schematic view illustrating the pulse area of the fluorescent light signal obtained from small cells such as fungi. As shown in FIG. 12A, the nucleus N1 of a large cell LC does not fit within the beam spot since the nucleus N1 of the large cell LC is larger than the width W of the beam spot. Therefore, the intensity of the fluorescent light signal reflects only part of the irradiated nucleus. However, the area value LA1, which integrates the fluorescent light signal intensity by time, can be considered a value that reflects the amount of nucleic acid of the entire nucleus. Hence, in the case of large cell LC, the area value LA1 which integrates the fluorescent light signal intensity by time is suitable as a parameter reflecting the amount of nucleic acid of the entire nucleus.

Conversely, in the case of small cells SC such as fungi, the entire nucleus N2 of the small cell SC fits within the beam spot since the nucleus N2 is smaller than the diameter W of the beam spot, as shown in FIG. 12B. In the case of small cells such as bacteria in particular, the entire particle fits within the beam spot. When the small cell SC advances in the flow direction, the entire nucleus N2 is irradiated in the time from the point at which the nucleus N2 enters the beam spot to the point at which the nucleus N2 leaves the beam spot. Therefore, when the area value LA2 which integrates the fluorescent light signal intensity by time is used as a parameter reflecting the amount of nucleic acid in the small cell SC, the apparent value is greater than the actual amount of nucleic acid. However, the fluorescent light intensity can be considered a value reflecting the actual amount of nucleic acid of the nucleus. In the case of a small cell SC, therefore, the fluorescent light intensity is suitable as a parameter reflecting the amount of nucleic acid.

In the sample analyzer 100 of the present embodiment, a first group of large cells including epithelial cells, atypical cells, and white blood cells, and a second group of small cells including spermatozoa, trichomonas, and fungi are discriminated (fractionation process), and the nucleated material components of the first group are classified using the fluorescence pulse area (first nucleated material classifying process), and the nucleated material components of the second group are classified using the fluorescent light intensity (second nucleated component classifying process). In the case of bacteria, the first group and the second group are detected separately (bacteria detecting process).

Figure 13:
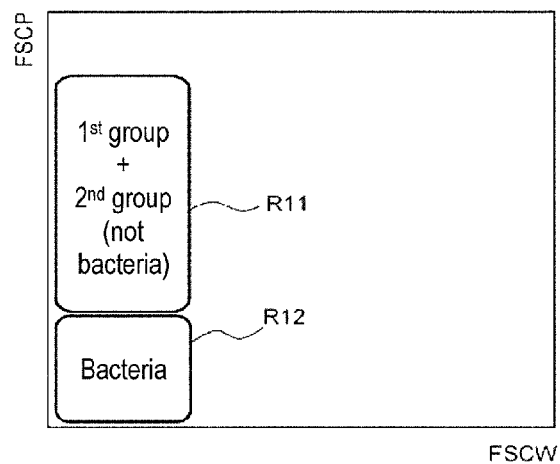
FIG. 13 shows the regions of appearance of the material components in the characteristic parameter space stipulated by the forward scattered light intensity and the forward scattered light pulse width.

In the fractionation process of S403, the particles of the second measurement sample are classified into a population including the first group and second group, and a bacteria population using the signals FSCP and FSCW. FIG. 13 shows the regions of appearance of the nucleated material components in the characteristic parameter space stipulated by the signals FSCP and FSCW. When the particles in the second measurement sample are plotted based on signals FSCP and FSCW, the nucleated material components of the first group and the second group are plotted in region R11 as shown in FIG. 13. The nucleated material component including bacteria is plotted in region R12. Note that particles plotted outside regions R11 and R12 are excluded from the analysis object as impurities.

Figure 14:
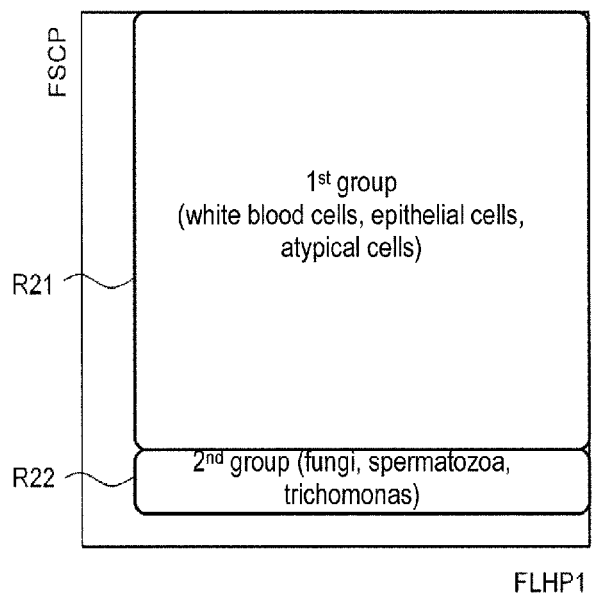
FIG. 14 shows the regions of appearance of the nucleated material components in the characteristic parameter space stipulated by the forward scattered light intensity and the first high sensitivity fluorescent light intensity.

The population of particles plotted in region R11 of FIG. 13 are classified into the first group and second group using signals FSCP and FLHP1. FIG. 14 shows the regions of appearance of the nucleated material components in the characteristic parameter space stipulated by the signals FSCP and FLHP1. The particle population plotted in region R11 of FIG. 13 are plotted in the characteristic parameters space stipulated by signals FSCP and FLHP1. The nucleated material component of the first group is plotted in region R21 shown in FIG. 14. The nucleated material component of group 2 is plotted in region R22.

In the first nucleated material component classifying process of S404, the particle population of the first group plotted in region R21 of FIG. 14 is classified into atypical cells, white blood cells, and epithelial cells using FSCW and FLLA to determine their numerical values.

Since atypical cells, white blood cells, and epithelial cells have higher amounts of nucleic acid than spermatozoa, *trichomonas*, and fungi, there is a large amount of fluorescent light generated when these particles are excited by irradiation. Therefore, the low sensitivity fluorescent light signal is suitable for analysis. Since the nucleus diameter is greater than the diameter of the beam spot, the fluorescence pulse area is suitable as a parameter. The atypical cells, white blood cells, and epithelial cells are classified using FLLA.

Figure 15:
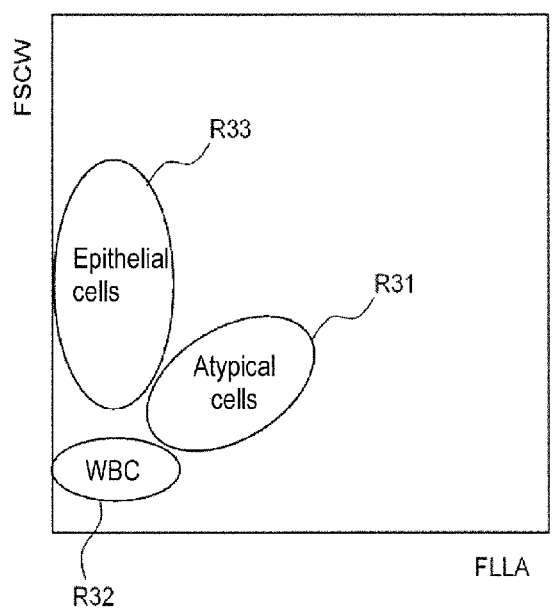
FIG. 15 shows the regions of appearance of the nucleated material components in the characteristic parameter space stipulated by the forward scattered light pulse width and the low sensitivity fluorescence pulse area.

FIG. 15 shows the region of appearance of the nucleated material components in the characteristic parameters space (referred to as the "FSCW-FLLA space" below) stipulated by FSCW and FLLA. The nucleated material components of the first group are plotted in the FSCW-FLLA space. As shown in the drawing, white blood cells, epithelial cells, and atypical cells have different FLLA distribution regions. This occurs because FLLA reflects the amount of nucleic acid, since there is generally no difference in the amount of nucleic acid in white blood cells and epithelial cells, and atypical cells have more nucleic acid than either white blood cells and epithelial cells. Moreover, the FSCW distribution regions are different for white blood cells and epithelial cells. This occurs because FSCW reflects the size of the particle and epithelial cells are larger than white blood cells. Particles plotted in region R31 are counted as atypical cells. Particles plotted in region R32 are counted as white blood cells (WBC). Particles plotted in region R33 are counted as epithelial cells.

Figure 16A:
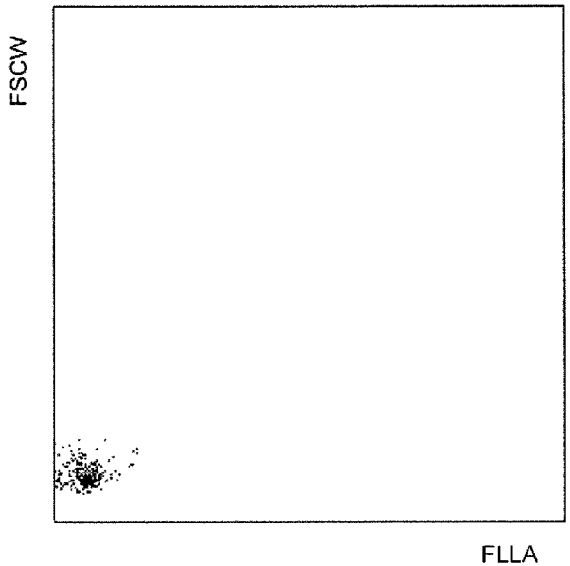
FIG. 16A is a scattergram showing an example of white blood cell detection results.
Figure 16B:
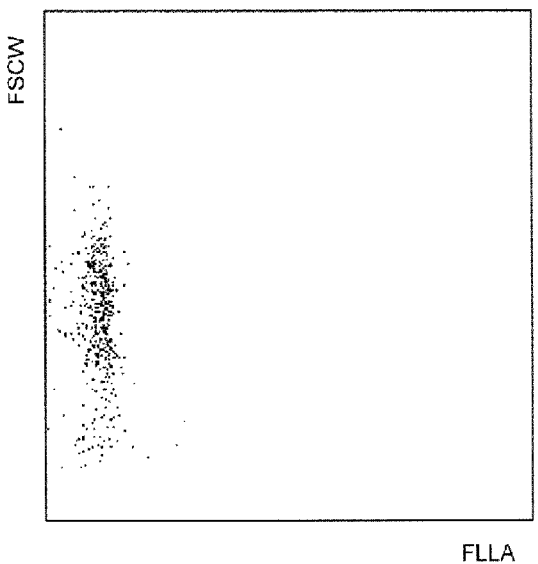
FIG. 16B is a scattergram showing an example of epithelial cell detection results.
Figure 16C:
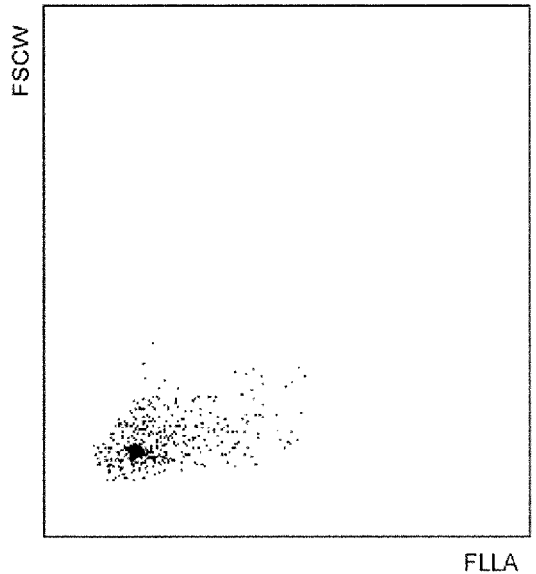
FIG. 16C is a scattergram showing an example of atypical cell detection results.

FIGS. 16A through 16C show the results of detecting actual nucleated components in the first nucleated component classifying process of S404. FIG. 16A is a scattergram showing an example of white blood cell detection results, FIG. 16B is a scattergram showing an example of epithelial cell detection results, and FIG. 16C is a scattergram showing an example of atypical cell detection results. Note than FIG. 16A shows results of measuring a sample containing white blood cells, FIG. 16B shows results of measuring a sample containing epithelial cells, and FIG. 16C shows results of measuring a sample containing atypical cells.

In the second nucleated component classifying process of S405, the particle population plotted in region R22 of FIG. 14 is classified as *trichomonas*, fungi, and spermatozoa using FSCP and FLHP1, and the respective numerical values are determined.

Since spermatozoa, *trichomonas*, and fungi have lower amounts of nucleic acid than white blood cells, epithelial cells and atypical cells, there is a relatively smaller amount of fluorescent light generated compared to cells of the first group when these particles are excited by irradiation. Therefore, the high sensitivity fluorescent light signal is suitable for analysis. Fluorescent light intensity is suitable as a parameter since the nucleus diameter is smaller than the diameter of the beam spot. Thus, spermatozoa, *trichomonas*, and fungi are classified using FLHP1.

Figure 17:
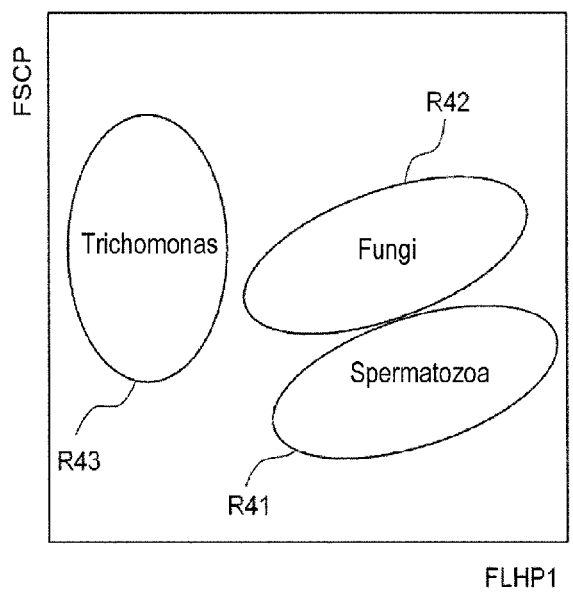
FIG. 17 shows the regions of appearance of the nucleated material components in the characteristic parameter space stipulated by the forward scattered light intensity and the first high sensitivity fluorescent light intensity.

FIG. 17 shows the regions of appearance of the nucleated material components in the characteristic parameter space stipulated by the signals FSCP and FLHP1. The nucleated material components of the second group are plotted in the characteristic parameter space stipulated by FSCP and FLIIP1. Spermatozoa, fungi and *trichomonas* have different distribution regions in the characteristic parameter space stipulated by FSCP and FLHP1. This occurs because the spermatozoa, fungi, and *trichomonas* are mutually different in size and nucleic acid content. Particles plotted in region R41 are counted as spermatozoa. Particles plotted in region R42 are counted as fungi. Particles plotted in region R43 are counted as *trichomonas*.

Figure 18A:
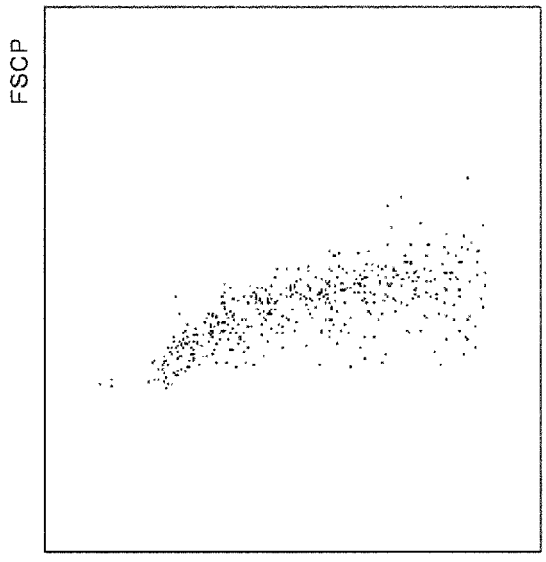
FIG. 18A is a scattergram showing an example of fungi detection results.
Figure 18B:
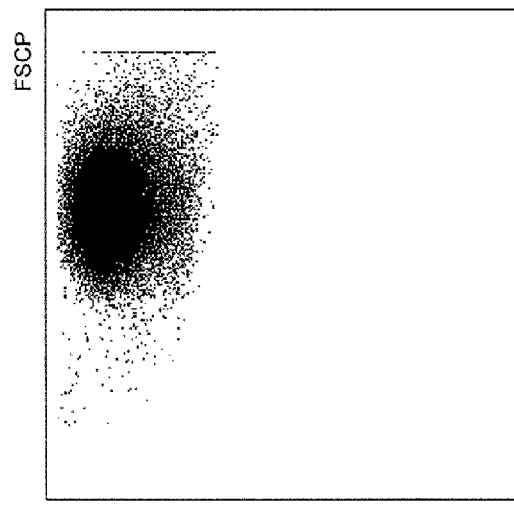
FIG. 18B is a scattergram showing an example of *trichomonas* detection results.
Figure 18C:
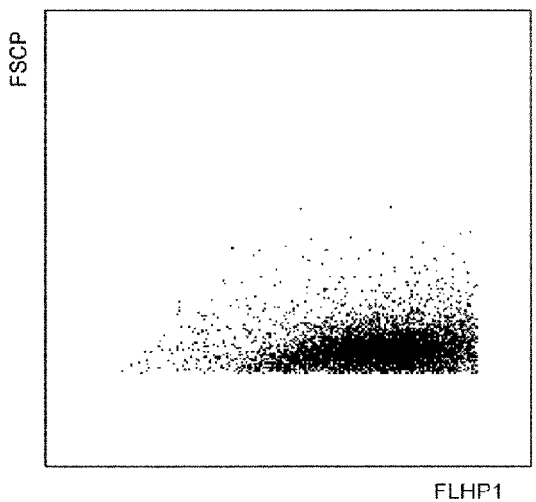
FIG. 18C is a scattergram showing an example of spermatozoa detection results.

FIGS. 18A through 18C show the results of detecting actual nucleated components in the second nucleated component classifying process of S405. FIG. 18A is a scattergram showing an example of fungi detection results, FIG. 18B is a scattergram showing an example of *trichomonas* detection results, and FIG. 18C is a scattergram showing an example of spermatozoa detection results. Note than FIG. 18A shows results of measuring a sample containing fungi, FIG. 18B shows results of measuring a sample containing *trichomonas*, and FIG. 18C shows results of measuring a sample containing spermatozoa.

In the bacteria detecting process of S406, bacteria are counted among the particle population plotted in region R22 of FIG. 14 using FSCP and FLHP2.

Figure 19:
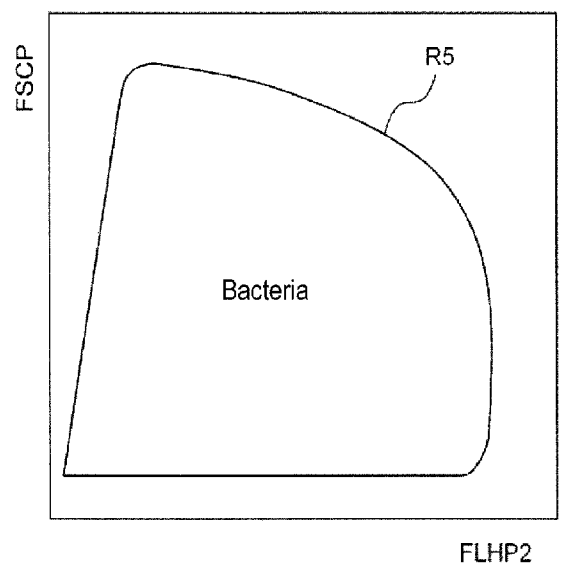
FIG. 19 shows the regions of appearance of the material components in the characteristic parameter space stipulated by the forward scattered light intensity and the second high sensitivity fluorescent light intensity.

Since bacteria are extremely small and have little nucleic acid compared to other nucleated cells such as white blood cells, the amount of fluorescence is slight compared to other cells. Bacteria also are much smaller than the diameter of the beam spot. Therefore, bacteria are detected using the signal FLHP2 which is the most sensitive and strong fluorescent light signal. FIG. 19 shows the regions of appearance of the bacteria in the characteristic parameter space stipulated by the signals FSCP and FLHP2. The particle population plotted in region R12 of FIG. 13 is plotted in the characteristic parameters space stipulated by signals FSCP and FLHP2. Bacteria appear in region R5 in the characteristic parameter space shown in FIG. 19. Note that although it is possible to plot nucleated cells other than bacteria in the characteristic parameter space shown in FIG. 19, the majority of nucleated cells are excluded from the analysis object due to saturation when converting to the high sensitivity fluorescent light signal. Non-nucleated impurities appear in the region of low fluorescent intensity outside region R5. Particles plotted in region R5 are counted as bacteria.

Figure 20:
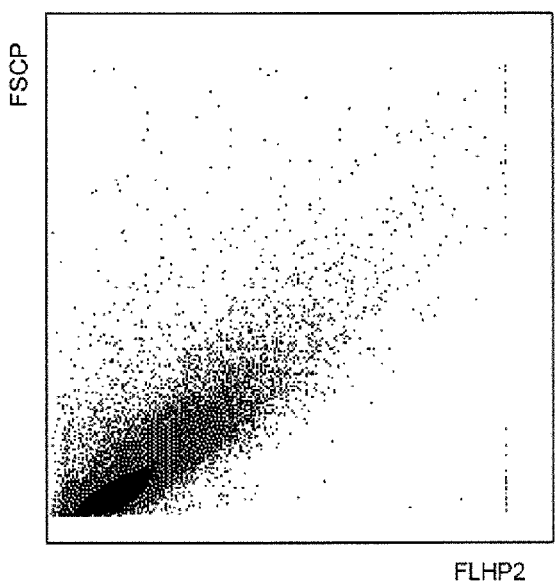
FIG. 20 is a scattergram showing an example of bacteria detection results.

FIG. 20 shows results when bacteria are actually detected in the bacteria detecting process of S406. FIG. 20 is a scattergram showing an example of bacteria detection results. Note that FIG. 20 shows results of measuring as sample containing bacteria.

The CPU 401 returns the process to the main routine when the measurement data analyzing process ends.

The CPU 401 displays the analysis results obtained by the measurement data analyzing process described above on the display section 409.

(Other Embodiments)

Note that although the above embodiment is described in terms of discriminating the first group and second group in the fractionation process, classifying the nucleated material components of the first group using FLLA in the first nucleated component classifying process, and classifying the nucleated material components of the second group using FLHP1 in the second nucleated component classifying process, the present invention is not limited to this configuration. That is, the particles plotted in a predetermined range of the characteristic parameter space are extracted, and it is unnecessary to repeat the process of plotting the extracted particles in the next characteristic parameter space. For example, the condition of identifying a single particle as a particular type of cell is defined as having a parameter within a range stipulated in the first characteristic parameter space, and a parameter within a range stipulated in the second characteristic parameter space. Such a condition is defined for each type of cell. A particle that meets any condition is identified as a cell type corresponding to that condition. By way of specific example, nucleated material components having FSCP and FLHP1 in R21 of FIG. 14, and having FSCW and FLLA in R32 of FIG. 15 are detected as white blood cells. Nucleated material components having FSCP and FLHP1 in R22 of FIG. 14, and having FSCP and FLHP2 in R5 of FIG. 19 are detected as bacteria. Cells of other types can be similarly identified.

Although the above embodiment is described by way of example of a two-dimensional characteristic parameter space, particles also may be plotted in a three-dimensional or high dimensionality characteristic parameter space.

Although the above embodiment has been described in terms of differentiating and detecting a first group and a second group mainly using different FSCP in the fractionation process, the present invention is not limited to this configuration. Parameters other than FSCP may be used as the parameters for identifying the first group and the second group insofar as the parameters reflect the nucleus diameter and size of the cell. For example, SSCP may be used instead of FSCP. The fluorescence pulse width also may be used instead of FSCP. Nucleated cells which have a nucleus diameter larger than the beam spot have a large fluorescence pulse width since the time from entering the beam spot to leaving the beam spot is longer than nucleated cells which have a nucleus diameter smaller than the beam spot. Accordingly, the first group and the second group also can be differentiated using the fluorescence pulse width.

In another embodiment, the DC impedance also may be used as a parameter reflecting the nucleus diameter or size of the cell. Specifically, the sample analyzer may be configured to incorporate a well known DC impedance device and flow cytometer. In this apparatus, the fluorescent signals of cells are obtained by the flow cytometer to obtain parameters reflecting the nucleus diameter and size of the cell by the DC impedance device.

Although the above embodiment is described in terms of classifying the first group of nucleated material components using FSCW and FLLA in the first nucleated component classifying process, the present invention is not limited to this configuration. FSCP or SSCP also may be used instead of FSCW.

Although the above embodiment is described in terms of classifying the second group of nucleated material components using FSCP and FLHP1 in the second nucleated component classifying process, the present invention is not limited to this configuration. For example, SSCP may be used instead of FSCP.

Although the above embodiment is described in terms of differentiating and detecting white blood cells, epithelial cells, and atypical cells in the first nucleated component classifying process, the present invention is not limited to this configuration. A configuration in which one or two cell types are detected from among white blood cells, epithelial cells, and atypical cells using the fluorescence pulse area also is possible. A further possible configuration detects one or two types from among spermatozoa, *trichomonas*, and fungi using fluorescent light intensity without differentiating and detecting spermatozoa, *trichomonas*, and fungi in the second nucleated component classifying process.

Although the above embodiment is described in terms of supplying staining liquid and diluting liquid separately to the reaction tank when preparing a measurement sample, the present invention is not limited to this configuration. A single reagent also may be supplied to the reaction tank when preparing a measurement sample when using a single reagent which contains both staining dye and diluting liquid components.

Although the above embodiment is described in terms of a sample analyzer which analyzes urine, the present invention is not limited to this configuration. The present invention also is applicable to sample analyzers which analyze liquid samples, and is applicable to sample analyzers which analyze urine and body fluids.

Although the above embodiment is described in terms of the sample distributing section 1 suctioning a fixed quantity of sample by pipetting and distributing aliquots of the sample to the reaction tank 2*u* and the reaction tank 2*b*, the present invention is not limited to this configuration. Another possible configuration dispenses fixed amounts of the suctioned sample by sampling valve, and the fixed amount aliquots are supplied to the reaction tank 2*u* and the reaction tank 2*b*.

Although the above embodiment is described in terms of sequentially executing a measurement sample preparing process, non-nucleated component measuring process, nucleated component measuring process, and measurement data analyzing process, this sequence is only an example inasmuch as the processes also may be executed in other sequences. For example, after preparing the first measurement sample, the non-nucleated component measuring process may be executed then the first non-nucleated component classifying process and second non-nucleated component classifying process are executed, and thereafter the second measurement sample is prepared, the nucleated component measuring process is executed, then the first nucleated component classifying process, second nucleated component classifying process, and bacteria detecting process are executed subsequently. A further possible modification is a sequence of measuring the second measurement sample using the first set value and measuring the second measurement sample using the second set value in the nucleated component measuring process.

Although the above embodiment is described in terms of analyzing measurement data in the information processing section, the present invention is not limited to this configuration. Measurement data also may be analyzed by the microcomputer 11 of the measuring unit 10.

What is claimed is:

1. A sample analyzer comprising:
   a sample preparing section configured to prepare a measurement sample by mixing a sample and a nucleic acid staining reagent;
   an optical detector configured to irradiate light on cells contained in the measurement sample, receive fluorescent light given off by the irradiated cells, and output fluorescent light signals;
   a signal processing section which obtains fluorescent light intensity and fluorescence pulse area of the cells from the fluorescent light signals output by the optical detector, the fluorescence pulse area integrating the fluorescent light signal intensity by time; and
   an information processing section configured to detect white blood cells, epithelial cells and atypical cells contained in the measurement sample based on the fluorescence pulse area, and detect bacteria contained in the measurement sample based on the fluorescent light intensity.

2. The sample analyzer of claim 1, wherein the information processing section is configured to further detect fungi contained in the measurement sample based on the fluorescent light intensity.

3. The sample analyzer of claim 1, wherein the information processing section is configured to further detect spermatozoa contained in the measurement sample based on the fluorescent light intensity.

4. The sample analyzer of claim 1, wherein the information processing section is configured to further detect trichomonas contained in the measurement sample based on the fluorescent light intensity.

5. The sample analyzer of claim 1, wherein the optical detector comprises:
a flow cell which forms the measurement sample into a sample flow; and
a light source configured to irradiate light formed into a beam spot on the flow cell;
wherein a diameter of the beam spot in a flow direction of the sample flow is 3 µm or greater but not exceeding 8 µm.

6. The sample analyzer of claim 1, wherein
the optical detector is configured to receive scattered light given off by the cells, and output scattered light signals; and
the information processing section is configured to detect the white blood cells contained in the measurement sample based on the fluorescence pulse area and parameters of the cells according to the scattered light signals.

7. The sample analyzer of claim 6, wherein the information processing section is configured to detect the bacteria contained in the measurement sample based on the fluorescent light intensity and the parameters of the cells according to the scattered light signals.

8. The sample analyzer of claim 1, wherein
the optical detector is configured to output fluorescent light signals at a first detection sensitivity, and a second detection sensitivity which is more sensitive than the first detection sensitivity; and
the information processing section is configured to detect the white blood cells based on the fluorescence pulse area of the fluorescent light signals output at the first detection sensitivity, and detect the bacteria based on the fluorescent light intensity of the fluorescent light signals output at the second detection sensitivity.

9. The sample analyzer of claim 1, wherein the sample is urine.

10. A sample analyzer comprising:
a sample preparing section configured to prepare a measurement sample by mixing a sample and a nucleic acid staining reagent;
a measuring section which comprises a light source and a flow cell, and forms a sample flow of the measurement sample within the flow cell irradiated by light from the light source to obtain fluorescent light intensity and florescence pulse area of cells contained in the measurement sample, and parameters reflecting size or nuclear diameter of the cells contained in the measurement sample; and
an information processing section configured to identify a type of cell having parameters above a predetermined value based on the fluorescence pulse area, and identify a type of cell with parameters below the predetermined value based on the fluorescent light intensity.

11. The sample analyzer of claim 10, wherein the information processing section is configured to:
identify cells that have parameters above the predetermined value, and that have a fluorescence pulse area within a specific range, as white blood cells, epithelial cells or atypical cells, and
identify cells that have parameters below the predetermined value, and that have a fluorescent light intensity within a specific range, as bacteria, fungi, spermatozoa, or trichomonas.

12. The sample analyzer of claim 10, wherein
the measuring section comprises:
a scattered light receiving unit which receives scattered light from the cells contained in the measurement sample and outputs scattered light signals, and
a fluorescent light receiving unit which receives fluorescent light from the cells contained in the measurement sample and outputs fluorescent light signals; and
the information processing section obtains the parameters reflecting the size or the nuclear diameter of the cells based on the scattered light signals.

13. A sample analyzing method comprising:
preparing a measurement sample by mixing a sample and a nucleic acid staining reagent;
flowing the prepared measurement sample through a flow cell and irradiating light on the flowing measurement sample in the flow cell;
outputting fluorescent light signals corresponding to fluorescent light given off by the cells in the measurement sample irradiated by light;
obtaining fluorescent light intensity and fluorescence pulse area of the cells from the fluorescent light signals;
detecting white blood cells contained in the measurement sample based on the fluorescence pulse area; and
detecting bacteria contained in the measurement sample based on the fluorescent light intensity.

14. The sample analyzing method of claim 13, further comprising detecting epithelial cells contained in the measurement sample based on the fluorescence pulse area.

15. The sample analyzing method of claim 13, further comprising detecting atypical cells different from the white blood cells and the epithelial cells contained in the measurement sample based on the fluorescence pulse area.

16. The sample analyzing method of claim 13, further comprising detecting fungi contained in the measurement sample based on the fluorescent light intensity.

17. The sample analyzing method of claim 13, further detecting spermatozoa contained in the measurement sample based on the fluorescent light intensity.

18. The sample analyzing method of claim 13, further detecting trichomonas contained in the measurement sample based on the fluorescent light intensity.

19. The sample analyzer of claim 1, wherein the information processing section is configured to further detect bacteria contained in the measurement sample based on the fluorescent light intensity.

* * * * *